(12) United States Patent
Panza

(10) Patent No.: US 8,697,659 B2
(45) Date of Patent: Apr. 15, 2014

(54) ANALOGUES OF GLYCOLIPIDS USEFUL AS IMMUNOADJUVANTS

(75) Inventor: Luigi Panza, Fino Mornasco (IT)

(73) Assignee: Luigi Panza, Fino Mornasco (IT)

( * ) Notice: Subject to any disclaimer, the term of this patent is extended or adjusted under 35 U.S.C. 154(b) by 455 days.

(21) Appl. No.: 12/734,140

(22) PCT Filed: Oct. 10, 2008

(86) PCT No.: PCT/IB2008/003263
§ 371 (c)(1),
(2), (4) Date: Oct. 29, 2010

(87) PCT Pub. No.: WO2009/060305
PCT Pub. Date: May 14, 2009

(65) Prior Publication Data
US 2011/0033485 A1    Feb. 10, 2011

Related U.S. Application Data

(60) Provisional application No. 60/979,785, filed on Oct. 12, 2007.

(51) Int. Cl.
*C07H 17/02* (2006.01)
*A61K 31/70* (2006.01)

(52) U.S. Cl.
USPC ............................................ 514/25; 536/17.9

(58) Field of Classification Search
None
See application file for complete search history.

(56) References Cited

U.S. PATENT DOCUMENTS 6,071,884 A * 6/2000 Koezuka et al. ................. 514/25
2007/0238871 A1    10/2007 Tsuji et al.

FOREIGN PATENT DOCUMENTS

| EP | 1437358 A1 | 7/2004 |
| EP | 1776963 A1 | 4/2007 |
| WO | WO-03/016326 A1 | 2/2003 |
| WO | WO-2005/000348 A2 | 1/2005 |
| WO | WO-2006/026389 A2 | 3/2006 |

OTHER PUBLICATIONS

Dumoulin et al., Journal of the American Chemical Society, 2002, 124, 13737-13748.*
Fujio et al. (Jan. 1, 2006). "Structure-based discovery of glycolipids for CD1d-mediated NKT cell activation: Tuning the adjuvant versus immunosuppression activity," J Amer Chem Soc 128(28):9022-9023.
International Search Report mailed Mar. 21, 2013, for PCT/IB2008/003263, 4 pages.
Wu et al. (Mar. 14, 2006). "Design of natural killer T cell activators: structure and function of a microbial glycosphingolipid bound to mouse CD1d," PNAS 103(11):3972-77.

* cited by examiner

*Primary Examiner* — Traviss C McIntosh, III
(74) *Attorney, Agent, or Firm* — Helen Lee; Otis Littlefield

(57) ABSTRACT

The invention provides analogs of alpha-galactosyl ceramide that increase the immune response elicited by various antigens. It also provides methods of using such compounds to increase the effectiveness of vaccines.

12 Claims, 4 Drawing Sheets

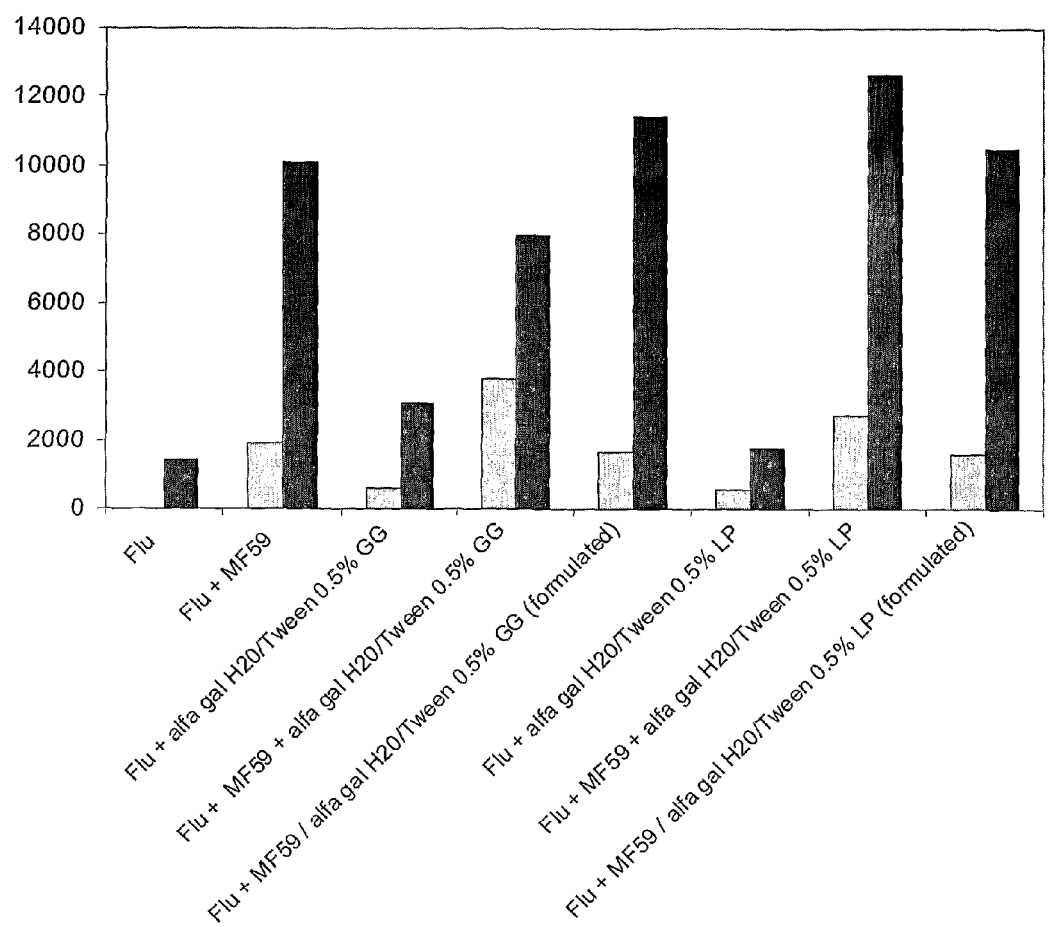

ANALOGUES OF GLYCOLIPIDS USEFUL AS IMMUNOADJUVANTS

RELATED APPLICATIONS

This application is the U.S. National Phase of International Application No. PCT/IB2008/003263, filed Oct. 10, 2008 and published in English, which claims priority to U.S. Provisional No. 60/979,785, filed Oct. 12, 2007. The teachings of the above applications are incorporated herein in their entirety by reference.

FIELD OF THE INVENTION

This invention relates to glycolipid analogues that are ligands for NKT cells (natural killer T-cells), methods of making them, and methods of using them as immunoadjuvants to increase the level of antibody titer upon vaccination.

BACKGROUND OF THE INVENTION

Glycolipids revealed recently a number of different immunological properties. Among them, it has been demonstrated that they can act as antigens when presented by CD1 molecules as well as that they can improve the immune response when administered in combination with a vaccine.

CD1 molecules are a family of highly conserved antigen presenting proteins similar in function to well known Major Histocompatibility Complex (MHC) molecules. While MHC proteins present peptides, CD1 proteins bind and display a variety of lipids and glycolipids to T lymphocytes.

In humans, the various CD1 isoforms are categorized as group I (CD1a, b, c and e) and group II (CD1d) based on sequence similarity [Calabi, F.; Jarvis, J. M.; Martin, L.; Milstein, C., Two classes of CD1 genes, *Eur. J. Immunol.* 1989, 19, (2), 285-92]. Crystal structures of human CD1a [Zajonc, D. M. et al, *Nat. Immunol.* (2003), 4, 808-815], hCD1b [Gadola, S. D. et al, *Nat. Immunol.* (2002), 3, 721-726], hCD1d [Koch, M.; et al *Nat. Immunol.* (2005), 6, 819-826.] and mouse CD1d (mCD1d) [Zeng, Z.-H. et al *Science* (1997), 277, 339-345; Zajonc, D. M. et al. *J. Exp. Med.* (2005), 202, 1517-1526], some in complex with their respective antigens, have revealed how differences in the topology of their respective binding grooves enable them to have a degree of ligand specificity, while maintaining the ability to present a diverse set of antigenic lipids.

In particular, mCD1d revealed an overall fold similar to the MHC class I proteins. The α-chain folds into three domains (α1, α2, and α3) and is closely associated with β2m. The membrane distal α1 and α2 domains form the binding groove, which is composed of an eight-stranded anti-parallel β-sheet floor traversed by two anti-parallel α-helices [Zeng, Z.-H. et al *Science* (1997), 277, 339-345]. It was further shown that mCD1d could accommodate long lipid tails in two hydrophobic pockets, designated A' and F', located in the binding groove. Moreover, the structures of hCD1b and hCD1a demonstrated that CD1, when loaded with antigenic glycolipids, binds the lipid portion in a hydrophobic groove while making available the hydrophilic sugar moiety to make contact with the T-cell receptor.

Mammalian and mycobacterial lipids are known to be presented by human CD1a, CD1b, CD1c and CD1d [Porcelli, S. A. & Modlin, R. L. (1999) *Annu. Rev. Immunol.* 17, 297-329]. Alpha-galactosyl ceramide (α-GalCer), a lipid found in the marine sponge *Agelas mauritianus*, has been, to date, the most extensively studied ligand for CD1d. α-GalCer, when bound to CD1d, stimulates rapid Th1 and Th2 cytokine production by Vα14z natural killer T cells (Vα14z NKT cells) in mice, and the human homologue Vα24z NKT cells and can be now considered as a model antigen. However, its physiological significance in mammals remains unclear, as it is enigmatic why an α-galactosyl ceramide of marine origin is such a potent agonist.

α-GalCer:

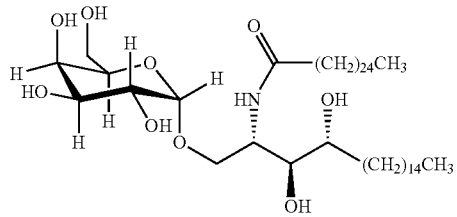

Natural Killer (NK) cells typically comprise approximately 10 to 15% of the mononuclear cell fraction in normal peripheral blood. Historically, NK cells were first identified by their ability to lyse certain tumor cells without prior immunization or activation. NK cells also serve a critical role in cytokine production, which may be involved in controlling cancer, infection and possibly in fetal implantation.

Administration of α-GalCer together with immunogenic proteins resulted in an enhanced CD4+ and CD8+ NKT cell response to soluble antigens through interaction with dendritic cells [Ian F. Hermans, I. F. et al., *J. Immunol.* (2003), 171, 5140-5147]. Administration of α-GalCer also enhanced B lymphocyte responses, eliciting higher frequencies of memory B cells and higher antibody levels in response to booster immunizations [Galli G. et al, *PNAS*, (2007), 104; 3984-3989]. It has been used to enhance the efficacy of certain peptidic antigens. WO 2005/000348.

SUMMARY OF THE INVENTION

The current invention relates to a new class of immunogenic compounds that are analogues of α-GalCer, corresponding to the general structure shown below and new synthetic methods for their preparation and their use to enhance the effectiveness of vaccines. These compounds provide improved pharmacokinetic properties over α-GalCer, and are similarly effective at increasing the immune responses when an antigen or vaccine is administered.

In one aspect, the invention relates to compounds of Formula I and compositions containing such compounds:

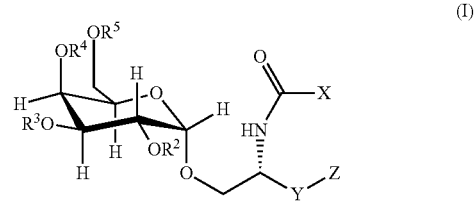

wherein $R^2$, $R^3$, $R^4$, and $R^5$ each independently represent H or a protecting group;

X is a C4-C30 hydrocarbyl group that can be substituted;

Y is a C1-C6 alkylene or C2-C6 alkenylene linker that can be substituted with up to two groups;

and Z is —$OR^1$, wherein $R^1$ is a C4-C20 hydrocarbyl group that can contain a heteroatom within its backbone, and is optionally substituted;

or a pharmaceutically acceptable salt thereof.

The compositions containing a compound of Formula I may be pharmaceutical compositions, and often include a pharmaceutically acceptable carrier. In some embodiments, the compositions further include at least one antigen, which is selected for its ability to elicit a desired immune response. Certain embodiments of the invention include a compound of Formula I admixed with a vaccine.

In another aspect, the invention relates to methods of making the compounds of Formula I, and to novel intermediates useful for making the compounds of Formula I.

In another aspect, the invention relates to methods of using the compounds of Formula I to enhance an immune response to an antigen, by administering a compound of Formula I to a subject who is exposed to the antigen. In specific embodiments, this method is useful to increase the effectiveness of a vaccine for administration to human subjects.

BRIEF DESCRIPTION OF THE FIGURES

FIG. 5 summarizes in vivo activity data for synthetic a-Gal GG and a-Gal LP as tested in an assay measuring IgG2a/IgG1 titers in Balb/C mice. IgG titers are shown in EU/ml. For each pair in the graph the columns represent, from left to right, IgG2a and IgG1.

DETAILED DESCRIPTION OF CERTAIN EMBODIMENTS

The Invention Compounds

Figure 1:
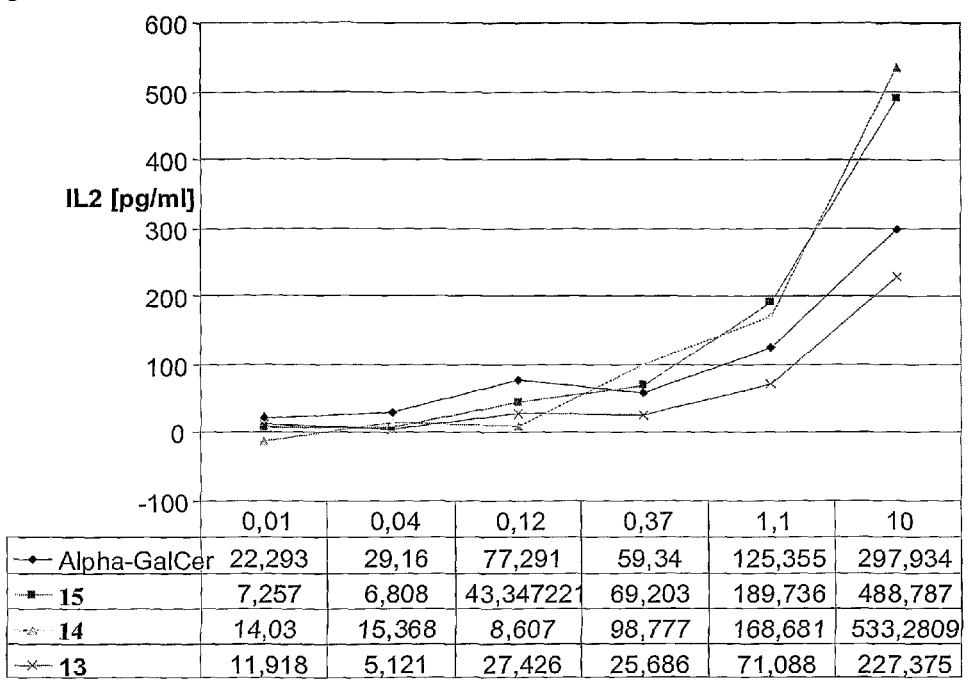
FIG. 1 demonstrates the activity of the synthetic compounds through activation of mouse T cell hybridomas FF13 when presented by APC (THP1). As a measure of T cell activation, IL2 release into the culture medium was determined after 48 hours culture by an ELISA assay. The y-axis shows IL2 levels in pg/ml. The x-axis is amount of glycolipid in µg/ml.

As used herein, "hydrocarbyl residue" refers to a residue which contains only carbon and hydrogen, unless otherwise specified. The residue may be aliphatic or aromatic, straight-chain, cyclic, branched, saturated or unsaturated, or any combination of these. The hydrocarbyl residue, when so stated however, may contain heteroatoms in addition to or instead of the carbon and hydrogen members of the hydrocarbyl group itself. Thus, when specifically noted as containing heteroatoms the hydrocarbyl group may contain heteroatoms within the "backbone" of the hydrocarbyl residue, and when optionally substituted, the hydrocarbyl residue may also have one or more carbonyl groups, amino groups, hydroxyl groups and the like in place of one or more hydrogens of the parent hydrocarbyl residue.

As used herein, "inorganic residue" refers to a residue that does not contain carbon. Examples include, but are not limited to, halo, hydroxy, $NO_2$ or $NH_2$.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C or as C1-C10 or C1-10. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described.

Typically, the alkyl, alkenyl and alkynyl substituents of the invention contain 1-10C (alkyl) or 2-10C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl and alkynyl groups are often substituted to the extent that such substitution makes sense chemically. Typical substituents include, but are not limited to, halo, =O, =N—CN, =N—OR, =NR, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', $NR'_2$, SR', $SO_2R'$, $SO_2NR'_2$, $NR'SO_2R'$, $NR'CONR'_2$, $NR'COOR'$, $NR'COR'$, CN, COOR', $CONR'_2$, OOCR', COR', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —(CH$_2$)$_n$— where n is 1-8 and preferably n is 1-4, though where specified, an alkylene can also be substituted by other groups, and can be of other lengths, and the open valences need not be at opposite ends of a chain. Thus —CH(Me)- and —C(Me)₂- may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, $R^7$ is alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group. Where a group that is described can contain optional heteroatoms within the backbone or alkyl chain, for example, the heteroatoms are selected from N, O and S, unless otherwise specified.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

"Halo", as used herein includes fluoro, chloro, bromo and iodo. Fluoro and chloro are often preferred.

"Amino" as used herein refers to NH₂, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

In one aspect, the invention provides compounds of Formula I:

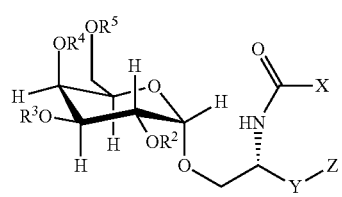

(I)

wherein $R^2$, $R^3$, $R^4$, and $R^5$ each independently represent H or a protecting group;

X is a C4-C30 hydrocarbyl group that can be substituted;

Y is a C1-C6 alkylene or C2-C6 alkenylene linker that can be substituted with up to two groups;

and Z is —OR¹, wherein $R^1$ is a C4-C20 hydrocarbyl group that can contain a heteroatom within its backbone, and is optionally substituted;

or a pharmaceutically acceptable salt thereof.

In Formula I, each of $R^2$, $R^3$, $R^4$, and $R^5$ can be H, or one or more of these can be a protecting group. In some embodiments, $R^2$ and $R^3$; or $R^3$ and $R^4$; or $R^4$ and $R^5$ can be joined together into a ring; for example, any of these pairs could represent an acetonide protecting group. 'Protecting group' includes the conventional acyl, alkyl, arylalkyl, silyl, and other groups typically used for protection of a hydroxyl during organic synthesis. Specific examples include methyl, formyl, acetyl, methoxyacetyl, trimethylsilyl, t-butyldimethylsilyl, methoxymethyl, 2-trimethylsilylethoxymethyl, benzyl, dimethoxybenzyl, allyl, methoxycarbonyl, allyloxycarbonyl, trichloroethoxycarbonyl, benzyloxycarbonyl, and the like. In particular, each of $R^2$, $R^3$, $R^4$, and $R^5$ can be an optionally substituted C1-C10 acyl group, such as formyl, acetyl, propionyl, pivaloyl, benzoyl, methoxycarbonyl, benzyloxycarbonyl or substituted benzyl-oxycarbonyl, t-butoxycarbonyl; or an optionally substituted arylmethyl group such as benzyl, methoxybenzyl, or dimethoxybenzyl. Compounds wherein one or more of $R^2$, $R^3$, $R^4$, and $R^5$ represents one of these protecting groups, and the remaining ones are each H, are particularly preferred, because they can serve as intermediates for the synthesis of further compounds of the invention, by modifications that are well known in the art including further deprotection; and they can also be administered as immunoadjuvants that act either directly or after in vivo conversion to a compound wherein each of $R^2$, $R^3$, $R^4$, and $R^5$ is H.

In formula I, X is preferably a straight chain or branched hydrocarbon having 4-30 carbons, and preferably it contains 10-30 carbons. Straight chain alkyl groups having 20-30 carbons are preferred, and a 25 carbon alkyl group is sometimes preferred. Frequently, X is an alkyl group, but in some embodiments it is an alkenyl group or an alkynyl group. X can be unsubstituted or it can be substituted with one or more suitable substituents for an alkyl group. Preferred substituents for X include halo, particularly F; and alkoxy, particularly C1-C6 alkoxy such as methoxy, ethoxy, isopropoxy, and the like.

Y can be a C1-C6 alkylene or a C2-C6 alkenylene, and can be unsubstituted or it can be substituted with one or more groups that are often selected from halo, C1-C6 alkyl, C1-C6 alkoxy, C1-C6 haloalkyl, and hydroxyl when Y is an alkylene. When Y is alkenylene, the preferred substituents include halo, C1-C6 alkyl, C1-C6 alkoxy, and C1-C6 haloalkyl. Where two substituents are present on Y, either on a single carbon or on adjacent connected carbons, the substituents can be joined together to form a ring having 5-6 members and optionally having up to two heteroatoms selected from N, O and S as ring members. In some embodiments, Y is $CH_2$ or $CH_2CH_2$ or $(CH_2)_3$ or $(CH_2)_4$, or a hydroxyl-substituted version of one of these. In other emdodiments, Y is —CH(OH)—CH(OH)—$CH_2$—. In certain embodiments, —Y—Z is represented by this formula:

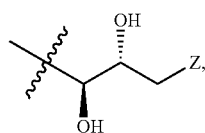

where Z is as defined above.

Z is a group —$OR^1$, wherein $R^1$ is a C4-C20 hydrocarbyl group that can contain a heteroatom within its backbone, which heteroatom is sometimes O and sometimes N or S, and $R^1$ can be unsubstituted or it can be substituted. Preferably, $R^1$ is a C4-C20 alkyl group that can be unsubstituted or it can be substituted, or it is a group of general formula —$(CH_2)_m$—O—$R^{1b}$, where m is 1-6 and $R^{1b}$ is a C1-C16 alkyl, cycloalkyl, or cycloalkylalkyl group, and $R^{1b}$ can be unsubstituted or it can be substituted with groups typically present on alkyl groups, such as hydroxyl, C1-C6 alkoxy, halo, and the like.

In some embodiments of Z, $R^1$ is a C1-C6 alkylene chain linked to a cycloalkyl or aryl or heteroaryl ring, e.g., a group of formula —$(CH_2)_r$-Rg where r is an integer from 1-6 and Rg represents a ring that can be a 3-8 membered alicyclic or heterocyclic ring, or a 5-10 membered aromatic or heteroaromatic group; and Rg can be substituted. Suitable examples include —$(CH_2)_{2-4}$-Rg, where Rg is a 3-8 membered monocyclic group, such as cyclopropyl, cyclopentyl, cyclohexyl, furanyl, tetrahydrofuranyl, pyranyl, tetrahydropyranyl, phenyl, pyridyl, pyrimidinyl, thienyl, and the like.

The invention also provides a novel synthetic approach that involves forming the glycosidic bond between galactose and the aglycone portion that attaches at the anomeric carbon of the galactosyl ring before the formation of the lipid portion of the sphingosine portion. It also provides useful intermediates of formula (IIa) and (IIb) for making the compounds of the invention. Thus in one aspect, the invention provides methods for making the compounds of formula I as described above, using intermediates of the general formula IIa or IIb:

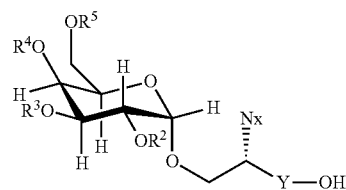

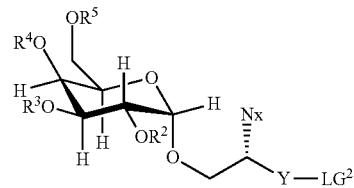

wherein Nx is a protected nitrogen group, such as $N_3$, NHC(O)X, NHC(O)J, or an imide such as succinimide or phthalimide; wherein J can be an optionally substituted C1-C10 alkyl or an optionally substituted C1-C10 alkoxy or optionally substituted benzyloxy group; and Y and $R^2$, $R^3$, $R^4$ and $R^5$ are as defined for Formula I.

For the compounds of Formula IIa and IIb, each of $R^2$-$R^6$ is preferably a protecting group, and not H. Preferred protecting groups include groups readily removed under reductive or hydrogenolytic conditions, such as benzyl, diphenylmethyl, benzyloxymethyl, benzyloxycarbonyl, and the like.

Certain compounds of the invention can be obtained from common intermediates of this type, as illustrated with compounds 7 and 10, using methods that are generally known in the art. The intermediates exemplified by compounds 7 and 10 are conveniently derived from a properly protected α-D-galactopyranosyl-(1-5)-lyxofuranose disaccharide, in which the lyxose moiety is the precursor of the polar part of the sphingosine analogue, as illustrated below. Other compounds of the invention can be made similarly, using alternative starting materials in place of the lyxofuranose, to provide intermediates such as IIa and IIb. These contain a group Nx that can be the acylamine —NHC(O)X of Formula I, or it can be a protected nitrogen such as azide (—$N_3$) or a succinimide or an acylated amine —NHC(O)J that can be converted into a free amine (—$NH_2$) or into the acylamine —NHC(O)X of Formula I by conventional methods. In these acylated amines, J can be an optionally substituted C1-C10 alkyl group, such as trifluoromethyl or trichloromethyl; or it can be an optionally substituted C1-C10 alkyoxy group, such as methoxy, ethoxy, 2,2,2-trichloroethoxy, or t-butoxy; or it can be an optionally substituted benzyloxy group such as benzyloxy, methoxybenzyloxy, dimethoxybenzyloxy and the like. These can be removed from nitrogen to provide a free amine ($NH_2$) by methods widely known in the art, and the free amine ($NH_2$) can then be acylated using conventional acylation conditions to introduce the —C(O)X group of Formula I. The azide can similarly be reduced and acylated as shown in the examples herein. Where Nx is an imide, it can be converted to the free amine by known methods such as treatment with hydrazine.

In one embodiment, the intermediates 7 or 10 can be alkylated at the free hydroxyl group or modified in any of numerous other ways to afford various compounds of the invention, containing various $R^1$ groups that can be linear or branched, saturated or unsaturated, and can contain aliphatic or aromatic rings, heteroatoms or various other functional groups. Representative examples of such methods include alkylation of an alcohol compound of formula IIa with an alkylating agent $R^1$-$LG^1$, and alkylation of an alcohol of formula $R^1$—OH with a compound of formula IIb, under known conditions such as Williamson ether conditions, where a base is used to promote the alkylation reaction, and Mitsunobu conditions, where a phosphine and an azodicarboxylate are typically used to promote the alkylation reaction.

In some embodiments, an intermediate of formula IIa is O-alkylated with an alkylating agent $LG^1$-$R^1$ to produce a compound of formula I. $R^1$ can be any of the groups described above for R1 in formula I. In other embodiments, an intermediate of formula IIb having a leaving group $LG^2$ is prepared, for example it can be made from a compound of formula IIa by conventional means such as sulfonation with a sulfonyl chloride or sulfonic anhydride, or conversion to a halide using known conditions such as $CBr_4$ and triphenylphosphine. The compound of formula IIb is then used to alkylate an alcohol of formula HO—$R^1$, providing a compound of formula I. $R^1$ in these reactions is as defined above, and can be in a protected form, if it comprises a free hydroxyl or free amine. $LG^1$ and $LG^2$ in these reactions represent conventional leaving groups, and are often selected from Cl, Br, I, and optionally substituted alkyl or aryl sulfonates, e.g., —$OSO_2$-J', where J' is optionally substituted C1-C10 alkyl or optionally substituted aryl. Suitable alkyl or aryl sulfonates that $LG^1$ and/or $LG^2$ can represent include, for example, mesylate (methanesulfonate), tosylate (toluenesulfonate), phenylsulfonate, trifluoromethylsulfonate (triflate), and the like.

While illustrated by schemes and examples using specific protecting groups on the galactose group, other protecting groups can be used instead as is well known in the art and discussed briefly herein. Suitable protecting groups and methods for installing and removing them are described in Wuts and Greene, *Protective Groups in Organic Synthesis*, 4th ed., Wiley Press (2006), which is incorporated herein by reference.

Scheme 1 illustrates the preparation of intermediate 7. Reagents and conditions: a) tri-(1-pyrrolidine)-phosphine oxide, b) i. tBuOK, DMSO, 80° C.; ii. $I_2$, pyridine/$H_2O$; c) $NaBH_4$, EtOH; d) PivCl, pyridine, DCM, r.t.; e) chloromethanesulfonyl chloride, pyridine; f) $NaN_3$, DMF, 85° C.; g) $Bu_4NOH$ (40% aq), dioxane. Scheme 1 is as follows:

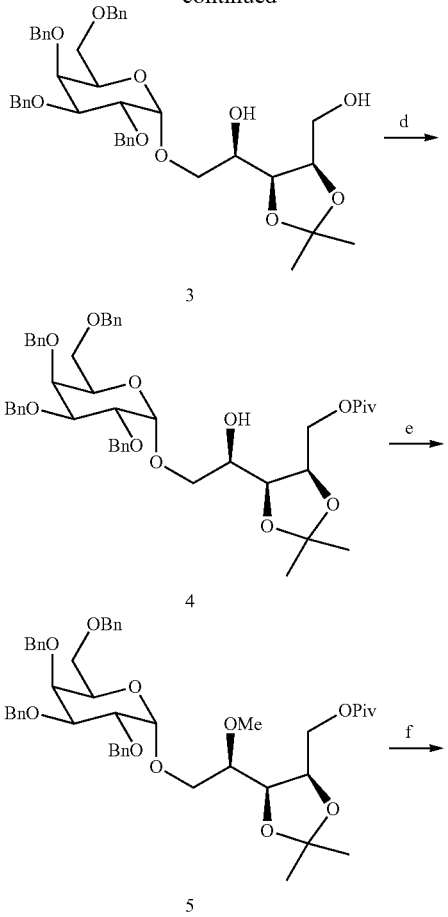

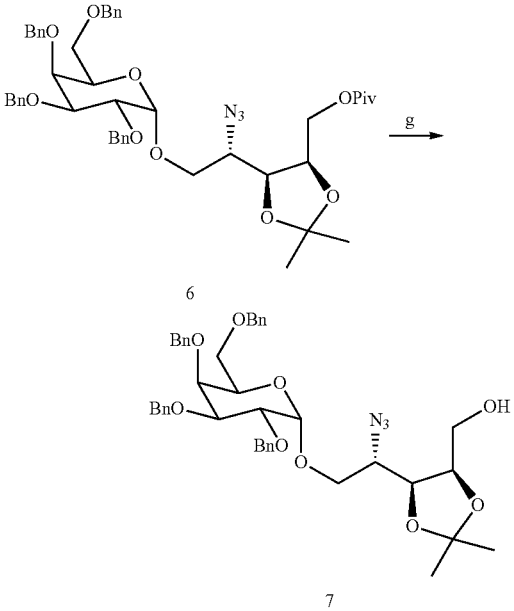

As one of ordinary skill would appreciate, various Y groups for compounds of formula I can be introduced by using other alcohols in place of the protected lyxose in the first step of Scheme 1. In particular, the use of other protected sugars can be used to introduce variations of Y having different relative or absolute stereochemistry from that provided by the lyxose shown in the Schemes.

Various compounds of the invention can be readily prepared from compound 7 by alkylation of the hydroxy group followed by reduction of the azide to an amine, where the amine can be acylated by conventional methods to install the —C(O)—X portion of the compound of Formula I. The benzyl protecting groups on the galactosyl ring can then be removed by hydrogenolysis or by other means such as TMSI; and the acetonide group can be removed under mild aqueous acid conditions as illustrated below and as known in the art. The order of these deprotection steps is not limited to the order recited. Where other protecting groups are used instead of Benzyl, they can be removed by conventional means as known in the art.

Scheme 2 illustrates the preparation of intermediate 10. Reagents and conditions: a) Lindlar catalyst, H$_2$, EtOH; b) hexacosanoic acid, EDC, HOBT, DIPEA; c) Bu$_4$NOH (40% aq), dioxane. Scheme 2 is as follows:

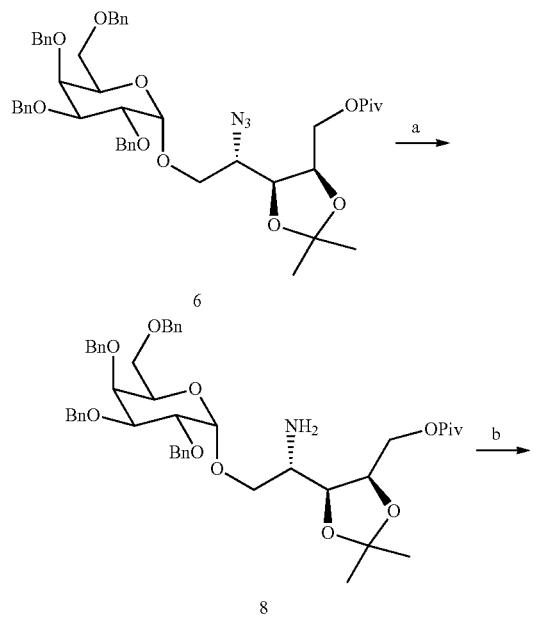

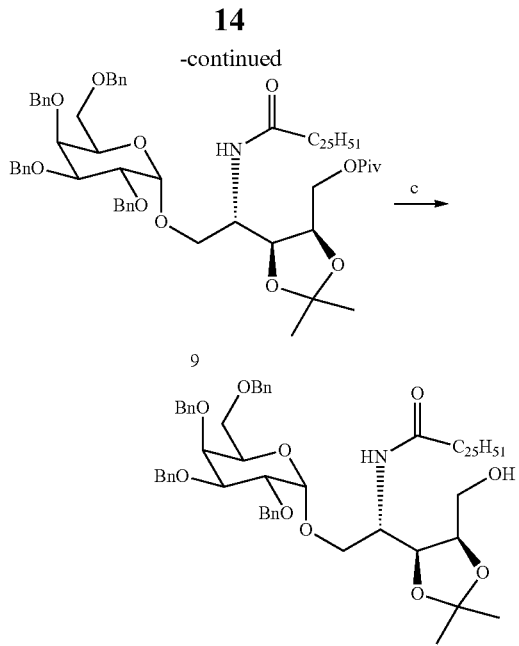

Similarly, compound 10 or an analog of compound 10 having a different X group can be used as a precursor for the synthesis of compounds wherein group Z is varied. Z can be introduced by a variety of known methods, most notably direct alkylation of the primary hydroxyl of compound 10 under basic conditions, using conventional alkylating agents such as alkyl halides or alkyl sulfates or alkyl sulfonates (e.g., mesylate or tosylate, etc.) Once the desired X and Z groups are installed, the compound can be deprotected as discussed above. Thus by using the methods illustrated herein, various compounds of the invention can be prepared.

Scheme 3 illustrates the use of the two common intermediates 7 and 10 to give certain oxa-analogues of α-GalCer by alkylation of the hydroxyl group, introduction of the fatty acid (only for 11) and final deprotection to provide selected compounds of Formula I.

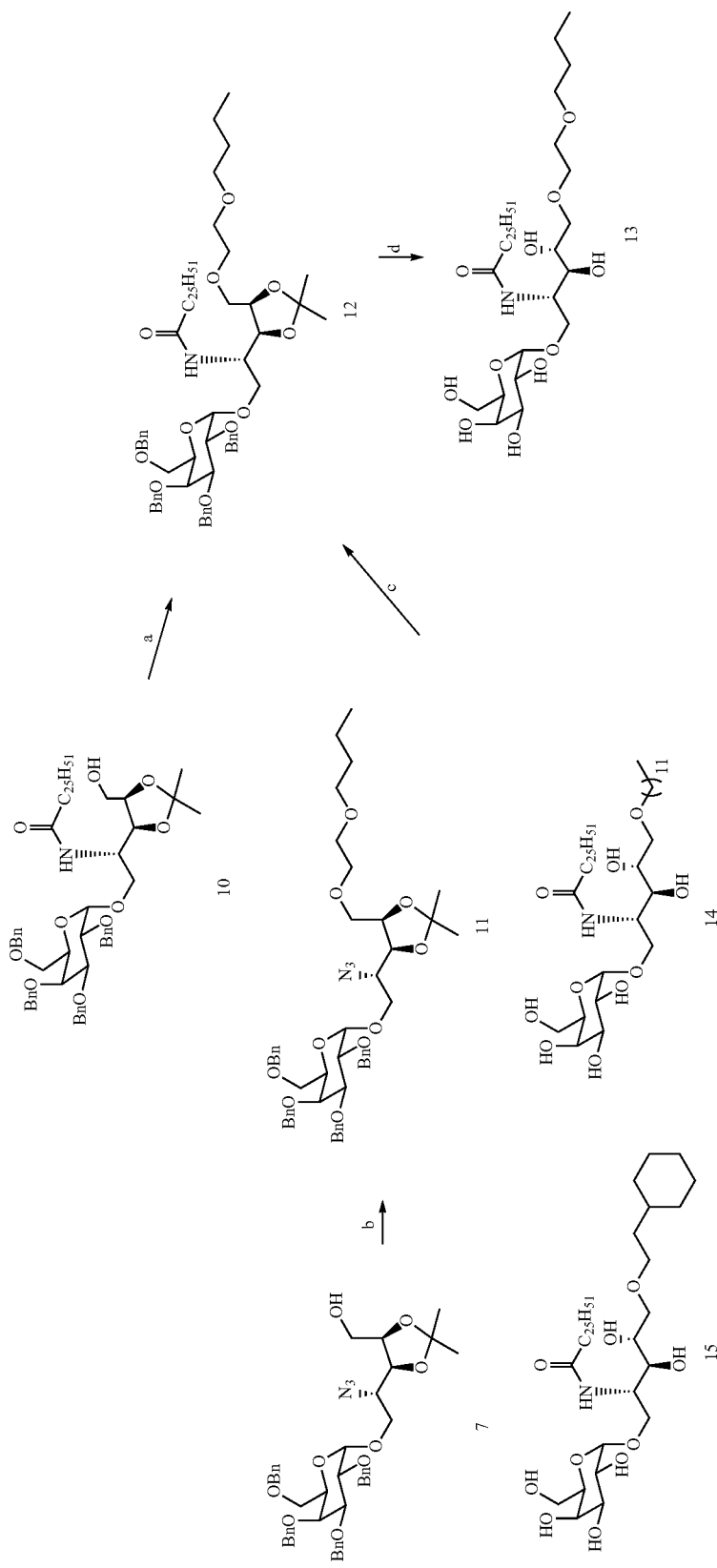

Reagents and conditions: a) KOH, 18-crown-6, nBuOCH$_2$CH$_2$OMs, THF; b) NaH, nBuOCH$_2$CH$_2$OMs, DMF; c) i. Lindlar catalyst, H$_2$, EtOH; ii. hexacosanoic acid, EDC, HOBT, DIPEA; c) i. 4 N HCl in dioxane, DCM-MeOH 5:1, ii. H$_2$, Pd(OH)$_2$/C, CHCl$_3$-MeOH 1:3.

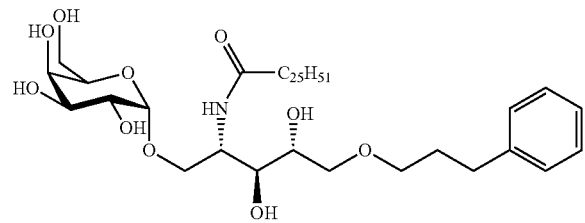

16

Compounds 14-16 were made similarly, using different alkylating agents for step (b). Other compounds of Formula I having different X, Y and Z groups are readily prepared by these methods using starting materials that are readily available in the art.

In some embodiment, the compounds of the invention are soluble in water and aqueous solutions. For example, compound 15 is soluble in water. In some embodiments, the compounds of the invention have a solubility of at least about 0.5 mg/mL, 1 mg/mL, 2 mg/mL, 5 mg/mL, 7.5 mg/mL, 10 mg/mL, 12.5 mg/mL, 15 mg/mL, 17.5 mg/mL, 20 mg/mL, 25 mg/mL, 30 mg/mL, 40 mg/mL, 50 mg/mL, 75 mg/mL, 100 mg/mL, 150 mg/mL or 200 mg/mL in an aqueous solution. In other embodiments, the compounds of the invention have improved aqueous solubility over other comparable compounds.

The biological evaluation of compounds of the invention uses mouse Vα14i NKT cells immortalized by cell fusion to give hybridomas FF13 through the presentation by APC (THP1). As a measure of T cell activation, IL2 release into the culture medium was determined after 48 hours culture by an ELISA assay.

The results showed that the synthetic glycolipid oxa-analogues of α-GalCer are able to stimulate significant release of IL2 when presented by APC to mouse hybridomas. Comparison with α-GalCer revealed that they have similar activities, and some of the novel compounds of the invention are more efficient. The replacement of a methylene group of α-GalCer by an oxygen atom does not interfere with the function of these compounds once they are loaded onto CD1d, and it can make them more viable for loading onto CD1d and improve their pharmacokinetic properties. Therefore, compounds of Formula I can be used in conjunction with at least one antigen to increase the immune response elicited by the antigen. Thus the compounds of the invention can be used in combination with one or more antigens that are used for vaccination to boost the potency of the antigen and of the vaccine.

Delivery Systems

Compositions of the invention may include at least one compound of Formula 1 admixed with one or more pharmaceutically acceptable excipients. Such compositions may be administered with a vaccine to vaccinate a subject, or they may be administered on the same day as a vaccine is administered to the subject to be vaccinated. Frequently the compound is admixed with an antigen or a vaccine, and the two are administered as a single dosage, whether by injection or ingestion or otherwise. Typically the compound will be administered as part of an antigen delivery system, and most typically it is admixed with an antigen or vaccine in a single composition, which may be any suitable vaccine composition. Suitable systems include emulsions, liposomes and microparticles. Thus a composition may comprise e.g. an oil-in-water emulsion to which the agonists described above have been added, liposomes containing the agonists described above, or microparticles containing and/or displaying the agonists described above.

Emulsions

Oil-in-water and water-in-oil emulsions are known for use in vaccines. O/W emulsions are preferred, and these typically include at least one oil and at least one surfactant, with the oil(s) and surfactant(s) being biodegradable (metabolisable) and biocompatible. The oil droplets in the emulsion are generally less than 5 μm in diameter, and may even have a sub-micron diameter, with these small sizes being achieved with a microfluidiser to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols, including any of the α, β, γ, δ, ε or ξ tocopherols can be used, but with α-tocopherols preferred (e.g. DL-α-tocopherol). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin or Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%. Specific oil-in-water emulsion adjuvants useful with the invention include, but are not limited to:

- A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59'. The MF59 emulsion advantageously includes citrate ions e.g. 10 mM sodium citrate buffer.
- An emulsion of squalene, a tocopherol, and Tween 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. Squalene and Tween 80 may be present volume ratio of about 5:2. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.
- An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL. The aqueous phase may contain a phosphate buffer.
- An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant (0.05-1% Thr-MDP, 5% squalane, 2.5% Pluronic L121 and 0.2% polysorbate 80). It can also be used without the Thr-MDP, as in the "AF" adjuvant (5% squalane, 1.25% Pluronic L121 and 0.2% polysorbate 80). Microfluidisation is preferred. Hariharan, et al., *Cancer Res*. Vol 55, 3486-89 (1995).
- An emulsion of squalene, a tocopherol, and a Triton detergent (e.g. Triton X-100). The emulsion may also include a 3d-MPL. The emulsion may contain a phosphate buffer.
- An emulsion having from 0.5-50% of an oil, 0.1-10% of a phospholipid, and 0.05-5% of a non-ionic surfactant. As described I WO 95/11700, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.
- A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, produced by addition of aliphatic amine to desacylsaponin via the carboxyl group of glucuronic acid), dimethyldioctadecylammonium bromide and/or N,N-dioctadecyl-N,N-bis (2-hydroxyethyppropanediamine.
- An emulsion in which a saponin (e.g. QuilA or QS21) and a sterol (e.g. a cholesterol) are associated as helical micelles. See WO2005/097181.
- An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer). See WO2006/113373
- An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer). See WO2006/113373.

Oil-in-water emulsions comprising squalene, with a submicron oil droplet diameter, are ideal.

Liposomes

Liposomes are vesicular structures based on lipid bilayers surrounding aqueous compartments. Various types of liposome are known in the art. They can vary widely in their physicochemical properties such as size, lipid composition, surface charge (cationic, neutral or anionic) and number and fluidity of the phospholipid bilayers. For instance, they may be composed of only phospholipids (neutral and/or negatively charged) and/or cholesterol. They may be mono- or multi-lamellar. Their use as adjuvants is described in e.g. U.S. Pat. No. 6,090,406; U.S. Pat. No. 5,916,588; EP-A-0626169.

Microparticles

Microparticles have been described for use as adjuvants e.g. see WO 98/33487 and Vaccine Adjuvants: *Preparation Methods and Research Protocols*, vol. 42 of *Methods in Molecular Medicine*, O'Hagan, ed. Preferred microparticles are made from biodegradable and non-toxic polymers. For instance, they may be made from a polymer selected from the group consisting of a poly(α-hydroxy acid), a polyhydroxy butyric acid, a polycaprolactone, a polyorthoester, a polyanhydride, and a polycyanoacrylate. Copolymers of these polymers can also be used e.g. or a copolymer of D,L-lactide and caprolactone.

Preferred polymers are poly(α-hydroxy acids), more preferably those selected from the group consisting of poly(L-lactide), poly(D,L-lactide) and poly(D,L-lactide-co-glycolide). The most preferred polymers are poly(D,L-lactideco-glycolide) polymers, referred to as 'PLG'. Preferred poly (D,L-lactide-co-glycolide) polymers are those having a lactide/glycolide molar ratio ranging from 25:75 to 75:25, more preferably 40:60 to 60:40 e.g. about 50:50. A 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component.

These polymers are available in a variety of molecular weights, and the appropriate molecular weight for a given antigen is readily determined by one of skill in the art. For polylactides, for example, a suitable molecular weight will be on the order of about 2000 to 5000. For PLG, suitable molecular weights will generally range from about 10,000 to about 200,000, preferably about 15,000 to about 150,000, and most preferably about 50,000 to about 100,000. A useful range is from 30,000 Daltons to 70,000 Daltons.

Microparticles can have a diameter in the range of ~100 nm to ~150 µm, more preferably ~200 nm to ~30 µm in diameter, and most preferably ~500 nm to ~10 µm in diameter. They will typically be substantially spherical.

Microparticles can be made in various ways. For example, double emulsion/solvent evaporation techniques are known, which involve the formation of a primary emulsion consisting of droplets of polymer solution, which is subsequently mixed with a continuous aqueous phase containing a particle stabilizer/surfactant. More particularly, a water-in-oil-in-water (w/o/w) solvent evaporation system can be used to form the microparticles. In this technique, the particular polymer is combined with an organic solvent, such as ethyl acetate, dimethylchloride (also called methylene chloride and dichloromethane), acetonitrile, acetone, chloroform, and the like. The polymer will be provided in about a 2-15%, more preferably about a 4-10% and most preferably, a 6% solution, in organic solvent. The polymer solution is emulsified using e.g. a homogenizer. The emulsion is then combined with a larger volume of an aqueous solution of an emulsion stabilizer such as polyvinyl alcohol (PVA) or polyvinyl pyrrolidone. The emulsion stabilizer is typically provided in about a 2-15% solution, more typically about a 4-10% solution. The mixture is then homogenized to produce a stable w/o/w double emulsion. Organic solvents are then evaporated. The formulation parameters can be manipulated to allow the preparation of small (<5 µm) and large (>30 µm) microparticles. For example, reduced agitation results in larger microparticles, as does an increase in internal phase volume. Particle size can be determined by routine methods.

As well as using double-emulsion techniques, single emulsion techniques can also be used. Microparticles can also be formed using spray-drying and coacervation, or by air-suspension coating techniques, such as pan coating and Wurster coating. Ionic gelation can also be used.

Following preparation, microparticles can be stored as they are, or can be freeze-dried for further use.

Microparticles can optionally be treated to have a negatively-charged surface (e.g. with SDS) or a positively-charged surface (e.g. with a cationic detergent, such as CTAB). Changes in surface characteristics can change the adsorption characteristics according to the antigen to be adsorbed.

Further Immunoactive Components

In addition to the compounds described herein, compositions of the invention may include additional immunostimulatory components. For instance, they may include one or more of the following: an aluminum salt; a calcium salt; a cytokine; a CD40 ligand; a saponin; and/or an immunostimulatory complex (ISCOM). In some embodiments, however, the composition contains no such additional immunostimulatory components.

Aluminum Salts

Aluminum salts may or may not be included in compositions of the invention. Suitable salts include the adjuvants known in the art as aluminum hydroxide and aluminum phosphate. These names are conventional, but are used for convenience only, as neither is a precise description of the actual chemical compound which is present. The invention can use any of the "hydroxide" or "phosphate" adjuvants that are in general use as adjuvants.

The adjuvants known as "aluminum hydroxide" are typically aluminum oxyhydroxide salts, which are usually at least partially crystalline. Aluminum oxyhydroxide, which can be represented by the formula AlO(OH), can be distinguished from other aluminum compounds, such as aluminum hydroxide $Al(OH)_3$, by infrared (IR) spectroscopy, in particular by the presence of an adsorption band at 1070 cm$^{-1}$ and a strong shoulder at 3090-3100 cm$^{-1}$. *Vaccine Design*, ch. 9. The degree of crystallinity of an aluminum hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminum hydroxide adjuvants. The pI of aluminum hydroxide adjuvants is typically about 11, i.e. the adjuvant itself has a positive surface charge at physiological pH.

The adjuvants known as "aluminum phosphate" are typically aluminum hydroxyphosphates, often also containing a small amount of sulfate (i.e. aluminum hydroxyphosphate sulfate). They may be obtained by precipitation, and the reaction conditions and concentrations during precipitation influence the degree of substitution of phosphate for hydroxyl in the salt. Hydroxyphosphates generally have a $PO_4$/Al molar ratio between 0.3 and 1.2. Hydroxyphosphates can be distinguished from strict $AlPO_4$ by the presence of hydroxyl groups. For example, an IR spectrum band at 3164 cm$^{-1}$ (e.g. when heated to 200° C.) indicates the presence of structural hydroxyls. VACCINE DESIGN: THE SUBUNIT AND ADJUVANT APPROACH (Powell & Newman, eds.), ch. 9, Plenum Press (1995).

The $PO_4/Al^{3+}$ molar ratio of an aluminum phosphate adjuvant will generally be between 0.3 and 1.2, preferably between 0.8 and 1.2, and more preferably 0.95±0.1. The aluminum phosphate will generally be amorphous, particularly for hydroxyphosphate salts. A typical adjuvant is amorphous aluminum hydroxyphosphate with $PO_4$/Al molar ratio between 0.84 and 0.92, included at 0.6 mg $Al^{3+}$/ml. The aluminum phosphate will generally be particulate (e.g. plate-like morphology as seen in transmission electron micrographs). Typical diameters of the particles are in the range 0.5-20 µm (e.g. about 5-10 µm) after any antigen adsorption.

The point of zero charge (PZC) of aluminum phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminum phosphates used according to the invention will generally have a PZC of between 4.0 and 7.0, more preferably between 5.0 and 6.5 e.g. about 5.7.

It is possible to use a mixture of both an aluminum hydroxide and an aluminum phosphate. In this case there may be more aluminum phosphate than hydroxide e.g. a weight ratio of at least 2:1 e.g. ≥5:1, ≥6:1, ≥7:1, ≥8:1, ≥9:1, etc.

The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

Calcium Salts

A composition of the invention may or may not include a calcium phosphate adjuvant. Various suitable forms of calcium phosphate are known, as described in more detail below.

*Vaccine Design*, Chapter 8, discusses how antigens can be adsorbed to calcium phosphate either by in situ precipitation of the salt in the presence of the antigens or by adsorption to a pre-formed salt.

Other known adjuvants include calcium phosphate. Rather than being strictly $Ca_3(PO_4)_2$, the adjuvants are reported to be non-stoichiometric hydroxyapatite of formula $Ca_{10-x}(HPO_4)_x(PO_4)_{6-x}(OH)_{2-x}$ and a pH-dependent surface charge with a point of zero charge (PZC) of 5.5. The adjuvants can form needle-like particles having dimensions of approximately 10 nm×150 nm as well as irregularly shaped plates having diameters of approximately 20-30 nm. Suitable calcium phosphate compositions are described, for example, in U.S. Pat. No. 5,676,976; WO 00/46147; WO 03/051394; and U.S. Pat. No. 6,355,271; and U.S. Pat. No. 5,851,670.

The Ca to P molar ratio of calcium phosphate adjuvants can vary e.g. between 1.35 and 1.83. The adsorption properties of the adjuvant have been found to vary depending on the conditions used during precipitation e.g. slow mixing may give an adjuvant with lower adsorption capacity that an adjuvant formed by quick mixing.

The amount of calcium phosphate, measured as $Ca^{++}$, may be between 0.1 mg/ml and 10 mg/ml e.g. between 0.5-5 mg/ml, preferably 0.75-3 mg/ml, 0.9-1.5 mg/ml, or about 1 mg/ml.

The calcium phosphate adjuvant has the capacity to adsorb antigens. For a given antigen, at least 80% (e.g. ≥85%, ≥90%, ≥92.5%, ≥95%, ≥97.5%, ≥97.5%, ≥98%, ≥99%, ≥99.5%, etc.) by weight of the total amount of that antigen is adsorbed. As calcium phosphate adjuvants are insoluble, typically particulate, the degree of adsorption can conveniently be measured by a method involving centrifugation and then determination of the amount of antigen in one (or both) of the solid or soluble material.

Antigens

The invention can be used with a variety of different antigens, including bacterial antigens, viral antigens, fungal antigens, protozoal antigens, tumor-related antigens, etc.

Bacterial antigens may be from bacteria including, but not limited to: as *Neisseria* (such as *N. meningitidis, N. gonorrhoeae*), *Streptococcus* (such as *S. agalactiae, S. pneumoniae, S. pyogenes, S. mutans*), *Staphylococcus* (such as *S. aureus*), *Corynebacterium diphtheriae, Clostridium* (such as *C. difficle, C. tetani*), *Vibrio cholerae, Mycobacterium* (such as *M. tuberculosis*), *Bordetella pertussis, Helicobacter pylori, Haemophilus influenzae, Borrelia burgdorferi, Chlamydia* (such as *C. trachomatis, C. pneumoniae*), *Yersinia pestis, Porphyramonas gingivalis, Moraxella catarrhalis.*

Protozoal antigens may be from protozoa including, but not limited to: *Plasmodium* (such as *P. falciparum, P. vivax, Pinalariae, P. ovale*).

Viral antigens may be from viruses including, but not limited to: hepatitis A virus, hepatitis B virus, hepatitis C virus, poliovirus, rabies virus, measles virus, mumps virus, rubella virus, varicella zoster virus, influenza virus, west nile virus, SARS coronavirus, human immunodeficiency virus, respiratoty syncytial virus, dengue virus, yellow fever virus, japanese encephalitis virus, tick-borne encephalitis virus, herpes simplex virus, epsten-barr virus, human cytomegalovirus, human papillomavirus.

Antigens may take various forms e.g. whole bacteria, whole virions, inactivated bacteria, inactivated virions, purified proteins, purified saccharides, glycoconjugates, etc. Rather than administer a protein, however, it is possible to administer a nucleic acid that will be translated in vivo to provide the protein in situ.

Where a saccharide antigen is used, it is preferably conjugated to a carrier protein in order to enhance immunogenicity. Any suitable conjugation reaction can be used, with any suitable linker where necessary.

In some embodiments, antigens may be conjugated to one of the immunopotentiators.

Pharmaceutical Compositions

Compositions of the invention are pharmaceutically acceptable. They may include components in addition to the immunopotentiators of formula I. they typically include one or more pharmaceutical carrier(s) and/or excipient(s). A thorough discussion of such components is available in REMINGTON: THE SCIENCE AND PRACTICE OF PHARMACY, $20^{th}$ ed. (2000).

Compositions will generally be in aqueous form, and frequently they will be isotonic. To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8.

The composition is preferably sterile. The composition is preferably non-pyrogenic e.g. containing <1 EU (endotoxin unit, a standard measure) per dose, and preferably <0.1 EU per dose. The composition is preferably gluten free. The composition may include preservatives.

Formulations may be prepared in a manner suitable for systemic administration. Systemic formulations include those designed for injection (e.g., intramuscular, intravenous, or subcutaneous injection) or may be prepared for transdermal, transcutaneous, transmucosal or oral administration. Injection methods include intravenous, intramuscular, subcutaneous, and other methods for internal delivery. Mucosal administration may be to any suitable mucosal surface. Systemic administration may include relatively noninvasive methods such as the use of suppositories, transdermal patches, transmucosal delivery and intranasal administration. Oral administration is also suitable. Suitable forms include syrups, capsules, tablets, and the like as in understood in the art. Selection of a particular route for a given subject is well within the ordinary level of skill in the art. For example, rectal delivery as a suppository is often appropriate where the subject experiences nausea and vomiting that precludes effective oral delivery. Transdermal patches are commonly capable of delivering a controlled-release dosage over several days, and are thus suitable for subjects where this is appropriate.

Methods of Treatment

Compositions of the invention are suitable for administration to human patients, and the invention provides a method of raising an immune response in a patient, comprising the step of administering a composition of the invention to the patient. This may involve either (a) administering a composition comprising both immunopotentiators and antigen(s), or (b) co-administering an antigen-free immunopotentiator composition with an antigen-containing composition.

The invention also provides a composition of the invention for use as a medicament.

The invention also provides the use of a combination of two or more immunopotentiators (as defined above) in the manufacture of a medicament for raising an immune response in a patient.

The invention also provides (i) a combination of two or more immunopotentiators, as defined above, and (ii) an antigen, for simultaneous separate or sequential use in immunization.

The invention also provides an antigen and an immunopotentiator, as defined above, for use in (a) the manufacture of a medicament for raising an immune response in a patient, or (b) a method of raising an immune response against the antigen in a patient.

The immune response raised by these methods and uses will generally include an antibody (a B cell response) response and/or a T cell response.

The invention may be used to raise a mucosal immune response e.g. including an IgA response, such as a secretory IgA response. Instead, or as well, an IgG response may be raised.

The following examples are presented to increase understanding of certain aspects and embodiments of the invention, but are not to be construed as limiting the scope of the invention.

Reagents

All chemicals were purchased as reagent grade and used without further purification. All solvents were dried over freshly activated 4 Å molecular sieves.

General Information

Reaction were monitored with analytical thin layer chromatography (TLC) on Merck silica gel plates 60 $F_{254}$, and visualized under UV (254) and/or by staining with 5% $H_2SO_4$ in MeOH, acidic ceric ammonium molibdate or $KMnO_4$. Flash column chromatography was performed on Macherey-Nagel 60 silica gel. NMR spectra were recorded on a 300 MHz NMR spectrometer at 25° C. Chemical shift (in ppm) was determined in deuterated solvents. $^{13}C$ attached proton test (APT) spectra were obtained on a 300 (75 MHz) spectrometer and were calibrated relative to deuterated solvents.

EXAMPLE 1

Synthesis of the Common Intermediate 7

Allyl 2,3,4,6-tetra-O-benzyl-α-D-galactopyranosyl-(1→5)-2,3-O-isopropylidene-α-D-lyxofuranoside (1)

To a solution of 5 g of 2,3,4,6-tetra-O-benzyl-α-D-galactopyranosyl bromide [Grayson, E. J. et al, *J. Org. Chem.* (2005), 70, 9740-9754] (8.34 mmol) and 1.5 g of allyl 2,3-O-isopropylidene-α-D-lyxofuranoside (6.42 mmol) in DCM 4.4 mL of tri-(1-pyrrolidine)-phosphine oxide (19.6 mmol) were added [Mukaiyama, T. and Kobashi, Y., *Chem. Lett.* (2004), 33, 10-11]. The mixture was stirred at r.t. for 24 h then was diluted with EtOAc and filtered over Celite. After evaporation of the solvent the crude was purified by careful flash chromatography (Toluene/EtOAc 95/5) affording 4.12 g of 1 (85%).

$^{1}H$ (CDCl$_3$): δ 7.50-7.19 (m, 20H), 5.92-5.77 (m, 1H), 5.33-5.13 (m, 2H), 5.01 (br s, 1H), 5.00-4.50 (m, 9H), 4.47 (d, J=11.8, 1H), 4.41 (d, J=11.8, 1H), 4.25 (dt, J=6.1, J=3.8, 1H), 4.13-3.83 (m, 7H), 3.58-3.51 (m, 2H); 1.40 (s, 3H), 1.26 (s, 3H). $^{13}C$ (CDCl$_3$): δ 139.01, 138.70, 138.00, 128.44, 128.40, 128.33, 117.51, 112.57, 105.00, 98.00, 85.15, 79.83, 79.03, 78.41, 75.07, 74.87, 73.44, 73.17, 73.08, 67.87, 26.17, 25.04. Anal. calcd for: $C_{45}H_{52}O_{10}$ (752.89) C, 71.79; H, 6.96. Found: C, 71.66; H, 6.88.

2,3,4,6-tetra-O-benzyl-α-D-galactopyranosyl-(1→5)-2,3-O-isopropylidene-D-lyxofuranose (2)

To a soln of 2,509 g (3.33 mmol) of 1 in 34 mL of dry DMSO under argon, 0.56 g (5 mmol) of tBuOK were added. The mixture was stirred for 1.5 h at 80° C. After cooling the mixture was diluted with EtOAc, the organic soln was washed with water (×1) and brine (×3), dried over sodium sulfate and evaporated. The residue was dissolved in 65 mL of THF and to the soln were added 13 mL of water, 1.1 mL of pyridine and 1.69 g (6.66 mmol) of iodine. After 3 h at r.t., the mixture was diluted with EtOAc, washed with 5% aq. sodium thiosulfate, 1N HCl, sat. soln of sodium bicarbonate, and water. The soln was dried with sodium sulfate and the solvent evaporated. Flash chromatography (Toluene/AcOEt 90/10) afforded 2.16 g of 2 (91%).

$^{1}H$ (CDCl$_3$): δ 7.49-7.20 (m, 20H), 5.35 (br s, 1H), 5.00-4.66 (m, 7H), 4.60-4.52 (m, 2H), 4.48-4.35 (m, 3H), 4.11-3.95 (m, 4H), 3.91-3.75 (m, 2H), 3.55-3.44 (br d, 2H), 3.40 (d, J=6.1, 1H), 3.28 (br s, 1H), 1.41 (s, 3H), 1.29 (s, 3H). $^{13}C$ (CDCl$_3$): 139.01, 138.75, 138.70, 128.44, 128.37, 112.60, 101.13, 98.39, 98.05, 96.83, 85.54, 79.13, 78.82, 73.50, 73.31, 73.10, 69.33, 69.03, 68.79, 66.50, 66.13, 60.57, 26.15, 25.94, 25.20, 25.00, 21.22, 20.92, 14.30. Anal. calcd for: $C_{42}H_{48}O_{10}$ (712.82) C, 70.77; H, 6.79. Found: C, 70.92; H, 6.61.

(2R,3S,4R)-3,4-O-isopropylidene-1-O-(2,3,4,6-tetra-O-benzyl-α-D-galactopyranosyl)-1,2,3,4,5-pentanepentol (3)

To a solution of 2.1 g (2.85 mmol) of 2 in 20 mL of EtOH, 140 mg (3.56 mmol) of sodium borohydride were added. The mixture was stirred for 2 hours at r.t. The mixture was diluted with EtOAc, washed with 1N HCl, sat. soln of sodium bicarbonate and water. The soln was dried with sodium sulfate and the solvent evaporated. Flash chromatography (DCM/MeOH 97:3) afforded 1.65 g of 3 (81%). 1H (CDCl3): 7.49-7.20 (m, 20H), 5.01-4.53 (m, 7H), 4.47 (d, J=11.8, 1H), 4.38 (d, J=11.8, 1H), 4.22-3.87 (m, 9H), 3.81-3.63 (m, 2H), 3.55-3.44 (m, 2H), 3.40 (dd, J=88.8, J=6.1, 1H), 2.99 (br s, 1H), 1.48 (s, 3H), 1.31 (s, 3H). $^{13}C$ (CDCl$_3$): 138.72, 138.55, 138.43, 128.53, 128.37, 128.35, 108.42, 104.53, 98.62, 79.11, 76.17, 74.96, 73.80, 73.65, 73.18, 70.03, 67.74, 61.28, 27.17, 25.18. Anal. calcd for: $C_{42}H_{50}O_{10}$ (714.84) C, 70.57; H, 7.05. Found: C, 70.32; H, 7.25.

(2R,3S,4R)-3,4-O-isopropylidene-5-O-pivaloyl-1-O-(2,3,4,6-tetra-O-benzyl-α-D-galactopyranosyl)-1,2,3,4,5-pentanepentol (4)

To a solution of 1,265 g (1.77 mmol) of 3 in 28 mL of dry DCM under argon at 0° C., 0.65 mL of pyridine and 0.66 mL (5.3 mmol) of pivaloyl chloride were added. The mixture was allowed to warm to r.t. and stirred overnight. After 26 hours the mixture was diluted with EtOAc, washed with 1N HCl, and brine (3×). The organic layer was dried with sodium sulfate and evaporated. Flash chromatography (Pet. ether/ EtOAc 75:25) afforded 1.22 g of 4 (86%). $^1$H (CDCl$_3$): δ 7.52-7.20 (m, 20 H, ArH) 4.83 (d, J=3.7, 1H), 4.92 (d, J=11.3 Hz, 1H), 4.81 (d, J=11.9 Hz, 1H), 4.80 (d, J=11.3 Hz, 1H), 4.72 (d, J=11.3 Hz, 1H), 4.65 (d, J=11.9 Hz, 1H), 4.55 (d, J=11.3 Hz, 1H), 4.47 (d, J=11.7 Hz, 1H), 4.39 (d, J=11.7 Hz, 1H), 4.26-4.32 (m, 3H), 4.20 (m, 1H), 4.03 (dd, J=3.7, 9.8 Hz, 1H), 3.99 (t, J=6.5 Hz, 1H), 3.95-3.88 (m, 2H), 3.87 (br m, 1H), 3.73 (dd, J=6.4 Hz, J=10.4 Hz, 1H), 3.55 (dd, J=5.8 Hz, J=10.4 Hz, 1H),); 3.51-3.41 (m, 2H), 2.70 (d, J=7.3 Hz, 1 H) 1.47 (s, 3H), 1.31 (s, 3H), 1.19 (s, 9H). $^{13}$C (CDCl$_3$); δ: 178.28, 138.84, 138.70, 138.61, 138.22, 128.55, 128.40, 128.21, 128.03, 127.84, 108.86, 98.57, 79.16, 76.57, 76.44, 75.27, 75.08, 74.89, 73.65, 73.60, 73.21, 70.73, 69.92, 69.18, 67.91, 63.74, 38.87, 27.33, 27.23, 25.19.

Anal. calcd for: C$_{47}$H$_{58}$O$_{11}$ (798.96) C, 70.65; H, 7.32. Found: C, 70.64; H, 7.44.

(2S,3S,4R)-2-azido-3,4-O-isopropylidene-5-O-pivaloyl-1-O-(2,3,4,6-tetra-O-benzyl-α-D-galactopyranosyl)-1,3,4,5-pentanetetrol (6)

To a solution of 1.21 g (1.52 mmol) of 4 30 mL of dry pyridine, under argon and cooled to 0° C., 1.6 mL (1.77 mmol) of chloromethanesulfonyl chloride were added. The reaction was allowed to warm to r.t and stirred for 5 hours. The mixture was diluted with EtOAc. The organic layer was washed with 1N HCl, sodium bicarbonate and brine, dried with sodium sulfate and evaporated. The crude was filtered through a short pad of silica gel and used for the next step without further purification.

The crude was dissolved in dry DMF (12 mL) under argon. Sodium azide (0.45 g) was added and the mixture was warmed at 85° C. After 2.5 hours the mixture was diluted with DCM, washed with water (3×) the organic layer dried with sodium sulfate and evaporated. Flash chromatography (Pet. ether/EtOAc 85:15) 0.85 g of 4 (72% over two steps).

$^1$H (CDCl$_3$): δ 7.48-7.20 (m, 20H), 4.98-4.39 (m, 9H), 4.38-4.27 (m, 2H), 4.24-4.16 (m, 2H), 4.14-4.03 (m, 2H), 4.01-3.91 (m, 3H), 3.74 (dd, J=10.7 Hz, J=5.8 Hz, 1H). 3.55-3.43 (m, 3H), 1.40 (s, 3H), 1.27 (s, 3H), 1.19 (s, 9H). $^{13}$C (CDCl$_3$); δ: 178.3, 138.9, 138.7, 138.1, 128.4, 128.3, 127.9, 127.7, 109.1, 98.9, 78.7, 76.6, 75.3, 74.9, 74.3, 73.5, 73.3, 73.0, 70.0, 69.2, 69.1, 62.5, 59.2, 38.9, 27.8, 27.3, 25.5. Anal. calcd for: C$_{47}$H$_{57}$N$_3$O$_{10}$ (823.97) C, 68.51; H, 6.97; N, 5.10. Found: C, 68.83; H, 6.71; N, 4.96.

(2S,3S,4R)-2-azido-3,4-O-isopropylidene-1-O-(2,3,4,6-tetra-O-benzyl-α-D-galactopyranosyl)-1,3,4,5-pentanetetrol (7)

To a solution of 0.5 g (0.6 mmol) of 6 in dioxane (20 mL) 1.7 mL of a soln of tetrabutylammonium hydroxide were added. The mixture was stirred for 72 hours, then diluted with EtOAc. The organic layer was washed with 1N HCl, brine, dried with sodium sulfate and evaporated. Flash chromatography (Pet. ether/EtOAc 70:30) of the crude afforded 0.35 g (78%) of 7.

$^1$H (CDCl$_3$): δ 7.56-7.26 (m, 20H), 4.96-4.52 (m, 7H), 4.47, (d, J=11.8, 1H), 4.39, (d, J=11.8, 1 H), 4.25-4.20 (m, 2H). 4.19-3.90 (m, 5H), 3.81 (dd, $_j$=10.1, J=2.4, 1H), 3.74-3.64 (m, 2H), 3.55-3.43 (m, 2H), 1.40 (s, 3H), 1.29 (s, 3H). $^{13}$C (CDCl$_3$); δ: 138.91, 138.38, 138.32, 137.56, 128.44, 128.34, 127.67, 109.01, 98.92, 78.74, 76.63, 76.52, 75.29, 74.82, 74.71, 73.54, 73.43, 72.92, 72.17, 69.92, 69.5, 61.14, 59.68, 27.52, 25.73. Anal. calcd for: C$_{42}$H$_{49}$N$_3$O$_9$ (739.85) C, 68.18; H, 6.68; N, 5.68. Found: C, 68.42; H, 6.41; N, 5.86.

EXAMPLE 2

Synthesis of the Common Intermediate 10

(2S,3S,4R)-2-(N-esacosanoylamino)-3,4-O-isopropylidene-5-O-pivaloyl-1-O-(2,3,4,6-tetra-O-benzyl-α-D-galactopyranosyl)-1,3,4,5-pentanetetraol (9)

To a solution of 0.5 g (0.6 mmol) of 6 in EtOH (40 mL) a catalytic amount of Lindlar catalyst was added and the mixture was stirred for 4.5 hours under a hydrogen atmosphere. 0.107 g di (15) 0.07). The mixture was diluted with DCM and filtered through celite living 0.5 g of the crude amine 8 which was used directly for the next step.

To a solution of compound 8 in 20 mL of a 3:1 mixture of dry DCM-DMF under argon at 0° C., 296 mg (0.75 mmol) of hexacosanoic acid were added. To the suspension were added EDC (145 mg, 0.75 mmol), HOBT (102 mg, 0.75 mmol) and finally a solution of DIPEA (0.26 ml, 1.5 mmol) in DCM. After 20 hours the mixture was diluted with EtOAc, washed with 1N HCl, sat. soln of sodium bicarbonate and brine, dried with sodium sulfate and the solvent evaporated. Flash chromatography (Pet. ether/AcOEt 80:20) afforded 534 mg of 9 (72% over two steps). $^1$H (CDCl$_3$): δ 7.56-7.26 (m, 20H), 6.43 (d, J=9.2 Hz, 1H), 4.96-4.55 (m, 6H), 4.85 (d, J=3.9 Hz, 1H) 4.48, (d, J=11.8, 1H), 4.36, (d, J=11.8, 1H), 4.28-3.80 (m, 10H), 3.62-3.50 (m, 2H); 3.35 (dd, J=9.8 Hz, J=5.5 Hz, 1H), 2.03 (t, J=7.3 Hz, 2H), 1.6-1.5 (m, 2H), 1.42 (s, 3H), 1.28 (s, 3H), 1.25-1.22 (m, 46H), 1.18 (s, 9H), 0.87 (t, J=6.7 Hz). $^{13}$C (CDCl$_3$); δ. 178.15, 172.95, 138.65, 138.39, 138.33, 137.51, 128.55, 128.50, 128.39, 128.18, 128.02, 127.91, 127.72, 127.60, 108.86, 99.94, 79.01, 76.85, 75.44, 74.73, 74.68, 74.28, 73.73, 73.06, 70.64, 70.17, 69.68, 62.83, 48.47, 38.78, 36.74, 32.01, 29.80, 29.68, 29.54, 29.46, 27.84, 27.27, 25.82, 25.55, 22.78, 14.22. Anal. calcd for: C$_{73}$H$_{109}$NO$_{11}$ (1176.65) C, 74.52; H, 9.34; N, 1.19. Found: C, 74.81; H, 9.47; N, 1.06.

(2S,3S,4R)-2-(N-esacosanoylamino)-3,4-O-isopropylidene-1-O-(2,3,4,6-tetra-O-benzyl-α-D-galactopyranosyl)-1,3,4,5-pentanetetraol (10)

Compound 10 was obtained as described for the preparation of compound 7 starting from 500 mg of 9. The product was purified by flash chromatography (Pet. Ether/EtOAc 50:50) affording 345 mg (76%) of compound 10. $^1$H (CDCl$_3$): δ 7.54-7.26 (m, 20H), 6.63 (m, 1H), 4.95-4.54 (m, 7H), 4.46, (d, J=11.6, 1H), 4.35, (d, J=11.6, 1H), 4.21-4.09 (m, 2H), 4.09-3.80 (m, 7H), 3.60-3.40 (m, 3H), 3.35 (dd, J=9.5 Hz, J=5.2, Hz, 1H), 2.44 (br s, 1H), 2.03 (m, 1H), 1.6-1.5 (m, 2H), 1.39 (s, 3H), 1.29 (s, 3H), 1.25-1.22 (m, 46H), 0.86 (t, J=6.7 Hz). $^{13}$C (CDCl$_3$); δ; 173.47, 138.52, 138.33, 138.28, 137.73, 128.61, 128.52, 128.40, 128.21, 128.03, 127.92, 127.73, 127.61, 108.35, 100.21, 78.96, 77.97, 74.98, 74.80, 74.60, 73.80, 73.01, 70.63, 69.98, 69.63, 61.04, 47.99, 36.68, 32.11, 29.81, 29.74, 29.62, 29.49, 28.34, 25.76, 25.36, 22.98, 14.24. Anal. calcd for: C$_{68}$H$_{101}$NO$_{10}$ (1092.53) C, 74.76; H, 9.32; N, 1.28. Found: C, 74.45; H, 9.21; N, 1.16.

EXAMPLE 3

Synthesis of the Oxa Analogues of α-GalCer (2S,3S,4R)-2-azido-5-(2-butoxyethyl)-3,4-O-isopropylidene-1-O-(2,3,4,6-tetra-O-benzyl-α-D-galactopyranosyl)-1,3,4,5-pentanetetraol (11)

To a solution of 100 mg (0.135 mmol) of 7 in dry DMF (3 mL) under argon, 60% NaH (11 mg, 0.27 mmol) and 2-buthoxyethyl mesylate (75 mg, 0.4 mmol) were added. The mixture was stirred at 100° C. for 2 hours. Other 2 eq of NaH and 2-buthoxyethyl mesylate were added. After other 2 hours the mixture was quenched with ammonium chloride (sat. soln) diluted with EtOAc, washed with water (4×), dried with sodium sulfate and evaporated. Flash chromatography (Pet. ether/AcOEt 80:20) gave 74 mg (65%) of 11.

$^1$H (CDCl$_3$): δ 7.51-7.18 (m, 20H), 4.94 (m, 1H), 4.86-4.50 (m, 6H), 4.47 (d, J=11.8 Hz, 1H), 4.36 (d, J=11.8 Hz, 1H); 4.33 (m, 1H), 4.15-3.94 (m, 6H), 3.80 (dd, J=10.4, J=4.3, 1H), 3.72-3.44 (m, 8H), 1.56 (m, 2H), 1.40 (s, 3H), 1.36 (m, 2H), 1.27 (s, 3H), 0.90 (t, J=7.2 Hz, 3H). $^{13}$C (CDCl$_3$): δ 138.97, 138.45, 138.37, 137.60, 128.36, 128.31, 127.66, 109.00, 98.91, 78.75, 76.67, 75.34, 74.81, 74.68, 73.53, 73.38, 72.81, 71.27, 70.96, 70.09, 69.64, 69.20, 69.06, 59.61, 32.00, 28.01, 26.00, 25.54, 14.89. Anal. calcd for: C$_{48}$H$_{61}$N$_3$O$_{10}$ (840.01) C, 68.63; H, 7.32; N, 5.00. Found: C, 68.81; H, 7.16; N, 4.83.

(2S,3S,4R)-5-O-(2-butoxyethyl)-2-(N-exacosanoylamino)-3,4-O-isopropylidene-1-O-(2,3,4,6-tetra-O-benzyl-α-D-galactopyranosyl)-1,3,4,5-pentaentetraol (12)

From 10: to a solution of 100 mg (92 mmol) of 10 10 mg of KOH and 20 mg (0.1 mmol) of 2-buthoxyethyl mesylate were added. The mixture was stirred at 40° C. for 20 hours then diluted with EtOAc. The organic layer was washed with brine, dried with sodium sulfate and evaporated. Flash chromatography (toluene/EtOAc 80:20) gave 75 mg (68%) of 12.

From 11: the same procedure described for the preparation of 9 from 6 was followed affording compound 12 in 69% yield.

$^1$H (CDCl$_3$): δ 7.52-7.25 (m, 20H), 6.42 (d, J=8.8 Hz, 1H), 4.94-4.87 (d, J=3.8, 1H), 4.82-4.55 (m, 6H), 4.44 (d, J=11.8 Hz, 1H), 4.38 (d, J=11.8 Hz, 1H), 4.21 (m, 1H), 4.14-3.88 (m, 6H), 3.63-3.28 (m, 9H), 2.03 (m, 2H), 1.81-1.48 (m, 4H), 1.43 (s, 3H), 1.32 (s, 1H), 1.27-1.10 (m, 46 H), 0.92-0.80 (m, 6H). $^{13}$C (CDCl$_3$): δ 172.84, 138.45, 138.37, 137.59, 128.49, 128.47, 128.05, 108.72, 99.62, 79.03, 76.70, 73.68, 73.56, 73.03, 71.05, 70.92, 65.34, 48.02, 36.79, 32.03, 31.77, 29.57, 29.46, 28.05, 25.89, 22.80, 19.35, 14.03. Anal. calcd for: C$_{74}$H$_{113}$NO$_{11}$ (1192.69) C, 74.52; H, 9.55; N, 1.17. Found: C, 74.31; H, 9.67; N, 1.09.

(2S,3S,4R)-5-O-(2-butoxyetil)-2-(N-exacosanoylamino)-1-O-(α-D-galactopyranosyl)-1,3,4,5-pentanetetraol (13)

To a solution of 70 mg (0.06 mmol) of 12 in 4 mL of dioxane at 0° C., 0.08 mL of 4N HCl in dioxane was added. The mixture was allowed to warm to r.t and stirred for 4 hours. The solvent was evaporated and the crude product submitted directly to the next step.

The crude was dissolved in 2 mL of a CHCl$_3$/MeOH mixture. 30 mg of 10% Pd(OH)$_2$/C were added and the mixture was stirred under a hydrogen atmosphere for 3 hours. The mixture was filtered through celite and the solvent was evaporated. Flash chromatography (DCM/MeOH 90:10) gave 29 mg (62% over two steps) of 13.

1H (CDCl$_3$/CD$_3$OD 1:1): δ 4.87 (d, J=2.9 Hz, 1H), 4.21 (m, 1H), 4.00-3.50 (m, 14H), 3.46 t, J=6.7 Hz, 2H), 3.30 (m, 2H), 2.18 (br t, J=7.3, 2H), 1.61-1.44 (m, 4H), 1.40-1.21 (m, 46H), 0.95-0.80 (m, 6H). $^{13}$C (CDCl$_3$/CD$_3$OD 1:1): δ 174.72, 99.82, 72.57, 72.00, 71.20, 70.94, 70.42, 70.38, 70.16, 69.84, 69.74, 68.90, 66.92, 61.66, 50.06, 36.32, 31.87, 31.46, 29.61, 29.49, 29.29, 25.85, 22.59, 19.08, 13.71, 13.51. Anal. calcd for: C$_{43}$H$_{85}$NO$_{11}$ (792.14) C, 65.20; H, 10.82; N, 1.77. Found: C, 64.91; H, 11.03; N, 1.61.

In a similar manner compounds 14 and 15 can be obtained.

EXAMPLE 4

IL-2 Secretion by Recognition of Glycolipids by a Murine NKT Cell Line

Glycolipids: all α-GalCer analogues were synthesized as described. α-GalCer was synthesized according to literature methods [Figueroa-Pérez, S. & Schmidt, R. R. (2000) Carbohydr. Res., 328, 95-102].

THP1 (Human acute monocytic leukemia cell line) overexpressing CD1d receptors were used as APC (antigen presenting cells) and were cultured in RPMI medium (glutamine 2 mM, NaPyruvate 1 mM, non essential amino acids 1%, kanamycin 100 μl/ml, FBS 10%, β-mercaptoethanol 0.01 mM).

CD1d reactive mouse T cells hybridoma FF13 secreting IL2 as response to activation was used for evaluation of compounds. FF13 cells were cultured in RPMI1640 medium (glutamine 2 mM, NaPyruvate 1 mM, non essential amino acids 1%, kanamycin 100 μl/ml, FBS 10%, β-mercaptoethanol 0.01 mM).

THP1 hCD1d (Human THP-1 cells transfected with human CD1D) and Mouse NKT-cell hybridoma FF13 was provided by the University Hospital Basel.

DMSO stock solution (1 mg/mL) of the compounds were prepared, and diluted to different concentrations: 10 μg/ml; 1.1 μg/ml; 0.37 μg/ml; 0.12 μg/ml; 0.04 μg/ml; 0.01 μg/ml.

FF13 Stimulation

In a 96 multiwell, THP1 (APC) in 90 μl of serum free medium (5×10$^4$ cells) were loaded with 10 μl of a solution of the compounds and incubated for 2 hours.

100 μl FF13 in complete medium were added (10×10$^4$ per well) and after 48 hours the tests were evaluated for IL2 production.

IL2 concentration is evaluated by ELISA using a primary monoclonal Anti-mouse IL-2 Antibody (R&D System), a biotinylated detection anti-mouse IL-2 Antibody (R&D System) and as color developer SIGMA FAST OPD. All tests were performed in triplicate using as standard a recombinant mouse IL2 (R&D System).

Figure 2:
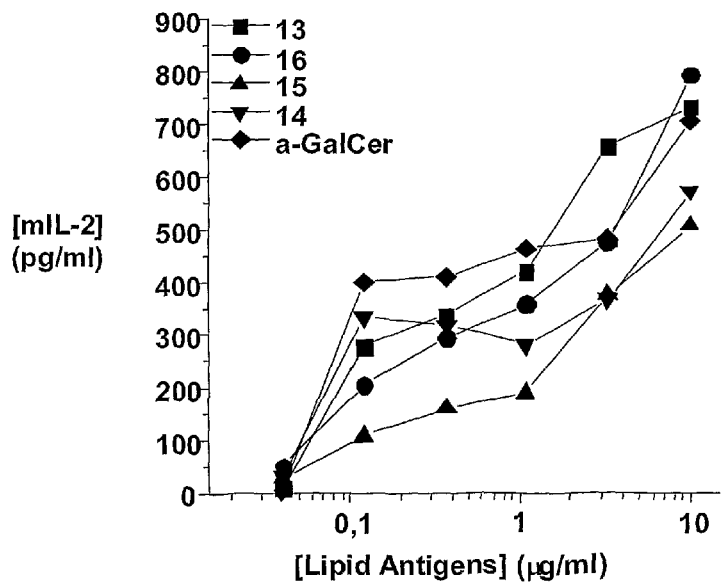
FIG. 2 summarizes activity data for four synthetic compounds as tested in an assay measuring IL-2 release by NKT hybridoma cells contacted with an APC exposed to the compounds or a-GalCer.

FIG. 2 depicts the IL2 levels released by cells that had been treated with compounds 13-16, compared to the effect of alpha-GalCer itself, in an NKT cell hybridoma test. The a-GalCer specific NKT hybridoma cells were added to CD1d-transfected THP-1 cells that had been exposed for two hours to various doses of the test compound (about 0.1 to about 10 μg/mL), and IL-2 levels in the medium were determined 48 hrs later. Compounds 13 and 16 were as effective as a-GalCer at 10 micromolar, and the other compounds were only a little less effective. Thus the oxygen inserted into the alkyl group of the ceramide compounds does not have a detrimental effect on activity, and significant variations of the alkyl group can be made with only modest changes in activity.

EXAMPLE 5

In Vivo Comparison Between Synthetic Alpha-Gal GG and Alpha Gal LP

Two different sources of synthetic α-GalCer were compared. In vivo comparison of the effects of synthetic "alpha-Gal GG" and "alpha-Gal LP" in the presence of influenza antigens were made in adult Balb/C mice. Both α-GalCer's were initially provided dissolved in $H_2O$ and 0.5% Tween 20. This Tween 20-dissolved material was administered either alone or in combination with a MF59 squalene-in-water emulsion. The α-GalCer's were either added to MF59 (non-formulated) or were incorporated into MF59 (formulated).

Groups of 8 adult mice (7 weeks) underwent 2 immunizations, 3 weeks apart. In addition, a group of mice were not administered any vaccine composition and used as a control. The immunization composition comprises an influenza antigen "Flu" and for each immunization, each mouse received 0.1 µg of A/Solomon H1N1, 0.1 µg of A/Wisconsin H3N2 or 0.1 µg of B/Malaysia influenza antigen. For mice treated with an a-GalCer, each mouse received 0.1 µg of an a-GalCer for each immunization. An immunization was administered by intramuscular injections of a 50 µL composition in the leg. Three weeks after the first administration, the second immunization was delivered wherein an additional 50 µL of the vaccine in a different leg was administered. Each of the following compositions were administered to a group of mice:
    Flu;
    Flu and MF59;
    Flu and a-Gal GG
    Flu and MF59 and a-Gal GG
    Flu and MF59 and a-Gal GG, formulated;
    Flu and a-Gal LP
    Flu and MF59 and a-Gal LP
    Flu and MF59 and a-Gal LP (formulated).

Figure 3:
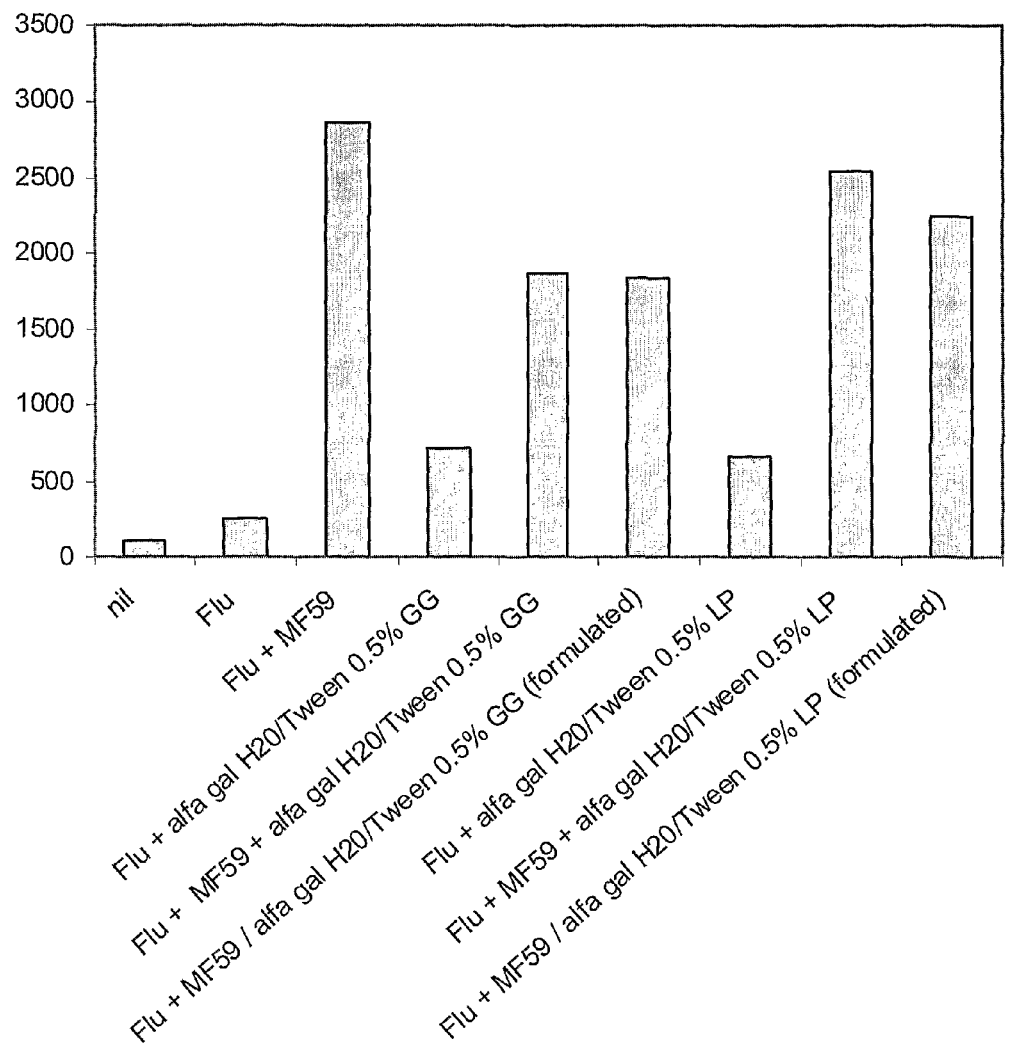
FIG. 3 summarizes in vivo activity data for synthetic a-Gal GG and a-Gal LP as tested in an assay measuring HI titers in Balb/C mice. Anti-H3N2 HI titers are shown.
Figure 4:
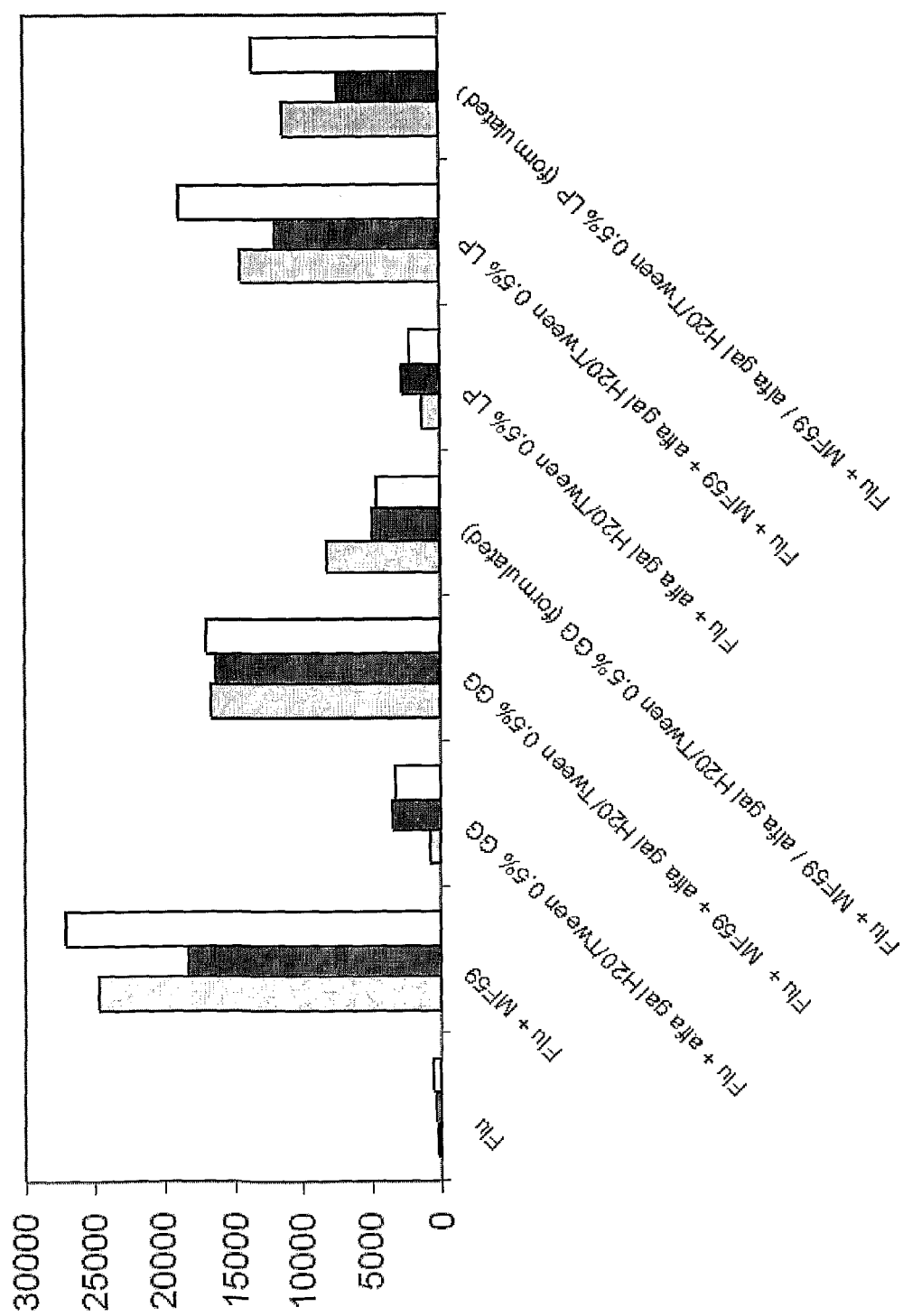
FIG. 4 summarizes in vivo activity data for synthetic a-Gal GG and a-Gal LP as tested in an assay measuring IgG titers in Balb/C mice. IgG titers are shown in EU/ml. For each triplet in the graph the columns represent, from left to right, B, H1N1 and H3N2.

The immune response to the vaccination composition was evaluated two weeks after the second immunization administration. Measurement of HI (hemagglutination-inhibition) titers and IgG titers was recorded and used as indicators of immune response. HI titers were measured using a HI assay and IgG titers are measured by ELISA. A summary of the results is found in FIGS. 3, 4 and 5 and show HI titers in response to H3N2 (A/Wisconsin), IgG titers in response to B (B/Malaysia), H1N1 (A/Solomon) and H3N2 (A/Wisconsin), and subclasses of IgG titers, respectively.

EXAMPLE 6

In Vivo Comparison Between Synthetic Alpha-Gal LP and its Derivatives

In vivo comparison of the effects of compounds a-Gal LP, 13, 14, 15 and 16 are made in adult Balb/C mice with influenza antigens. Compounds 13-16 are synthesized as described in the specification.

Groups of 8 adult mice (7 weeks) undergo 2 immunizations, 3 weeks apart. In addition, 4 mice are not administered any vaccine composition and used as a control group. The immunization composition comprises an influenza antigen "Flu" including 0.1 µg of hemagglutinin from each of the 2008/09 strains i.e. A/Brisbane/59/2007-like, A/Brisbane//10/2007-like and B/Florida/4/2006-like. For mice to be treated with an a-GalCer, each mouse receives 0.1 µg of an a-GalCer for each immunization. An immunization is administered by intramuscular injections of a 50 µL composition in the leg. Three weeks after the first administration, the second immunization is delivered wherein an additional 50 uL composition in a different leg is administered. Each of the following compositions are administered to a group of mice:
    Flu;
    Flu and MF59 adjuvant;
    Flu and a-Gal LP
    Flu and Compound 13 ($H_2O$/Tween 20 0.5%), 14 ($H_2O$/Tween 20 0.5%), 15 ($H_2O$), or 16 ($H_2O$/Tween 20 0.5%);
    Flu and MF59/a-Gal LP; and
    Flu and MF59/Compound 13, 14, 15, or 16.

The immune response to the vaccination composition is evaluated two weeks after the second immunization administration. Measurement of HI (hemagglutination-inhibition) titers, IgG and IgG subclass titers are recorded and used as indicators of immune response. HI titers are measured using a HI assay and IgG titers are measured by ELISA.

What is claimed:

1. A compound of formula I:

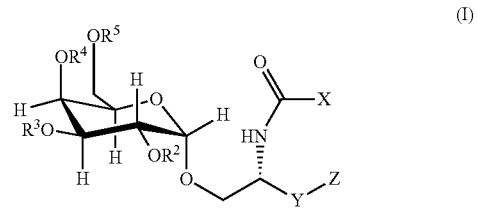

(I)

wherein $R^2$, $R^3$, $R^4$, and $R^5$ each independently represent H or a protecting group;

X is a C4-C30 hydrocarbyl group that can be substituted;

Y is a C1-C6 alkylene that can be substituted with up to two groups independently selected from halo, C1-C6 alkoxyl, C1-C6 haloalkyl, and hydroxyl or a C1-C6 alkylene or C2-C6 alkenylene linker that can be substituted with up to two groups, wherein each of the two groups does not result in an alkyl chain that extends longer than the C1-C6 alkylene or C2-C6 alkenylene linker; and Z is —$OR^1$, wherein $R^1$ is a C4-C20 hydrocarbyl group that can contain a heteroatom within its backbone, and is optionally substituted;

or a pharmaceutically acceptable salt thereof.

2. The compound of claim 1, wherein X is an unsubstituted alkyl group having 10-30 carbons.

3. The compound of claim 1 or 2, wherein Y is optionally substituted C3 alkylene optionally substituted with up to two groups independently selected from halo, C1-C6 alkoxy, C1-C6 haloalkyl, and hydroxyl.

4. The compound of claim 3, wherein —Y—Z is

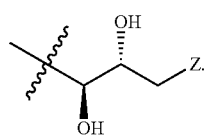

5. The compound of claim 1, wherein Z is —O—$R^1$, where $R^1$ is a C4-C20 hydrocarbyl.

6. The compound of claim 1, wherein Z is —O—$R^1$, where $R^1$ is $(CH_2)_m$—O—$R^{1b}$, where m is 1-6 and $R^{1b}$ is C1-C16 alkyl, cycloalkyl, or cycloalkylalkyl.

7. The compound of claim 1, wherein each of $R^2$, $R^3$, $R^4$ and $R^5$ is H.

8. The compound of claim 1, which is selected from the group consisting of

13

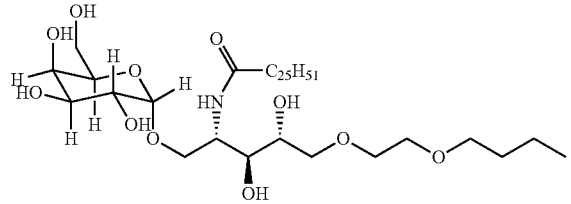

14

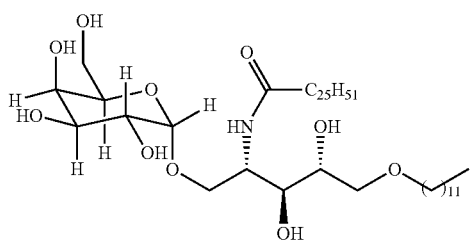

15

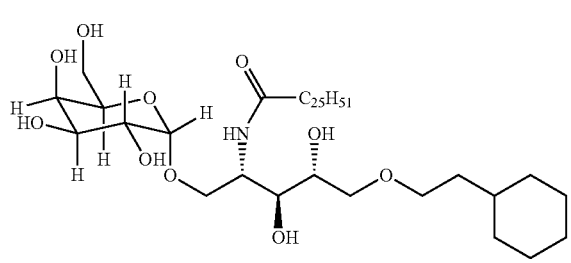

and

16

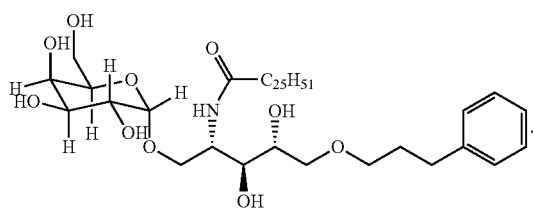

9. An immunogenic composition comprising a compound of Formula I:

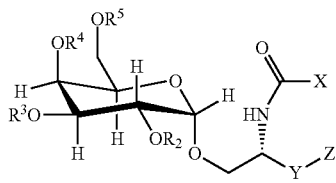

(I)

wherein $R^2$, $R^3$, $R^4$, and $R^5$ each independently represent H or a protecting group;

X is a C4-C30 hydrocarbyl group that can be substituted;

Y is a C1-C6 alkylene or C2-C6 alkenylene linker that can be substituted with up to two groups; and Z is —$OR^1$, wherein $R^1$ is a C4-C20 hydrocarbyl group that can contain a heteroatom within its backbone, and is optionally substituted; or a pharmaceutically acceptable salt thereof and an antigen.

10. A method to increase the immune response elicited by an antigen, comprising administering to a subject receiving the antigen an effective amount of a compound of Formula I:

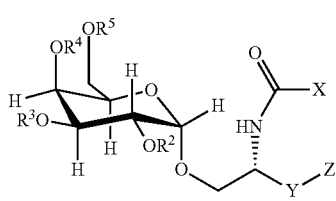

(I)

wherein $R^2$, $R^3$, $R^4$, and $R^5$ each independently represent H or a protecting group;

X is a C4-C30 hydrocarbyl group that can be substituted;

Y is a C1-C6 alkylene or C2-C6 alkenylene linker that can be substituted with up to two groups; and Z is —$OR^1$, wherein $R^1$ is a C4-C20 hydrocarbyl group that can contain a heteroatom within its backbone, and is optionally substituted; or a pharmaceutically acceptable salt thereof.

11. The method of claim 10, wherein the antigen and the compound of Formula I are administered at the same time or on the same day.

12. The method of claim 10, wherein the antigen is selected from bacterial antigens, viral antigens, fungal antigens, protozoal antigens, and tumor-related antigens.

* * * * *